US00PP09376P

United States Patent [19]

Christensen

[11] Patent Number: Plant 9,376

[45] Date of Patent: Nov. 21, 1995

[54] HYBRID TEA ROSE PLANT NAMED 'JACBOY'

[75] Inventor: Jack E. Christensen, Ontario, Calif.

[73] Assignee: Bear Creek Gardens, Inc., Medford, Oreg.

[21] Appl. No.: 324,410

[22] Filed: Oct. 17, 1994

[51] Int. Cl.[6] ..... A01H 5/00

[52] U.S. Cl. ..... Plt./12

[58] Field of Search ..... Plt./11, 12

[56] References Cited

U.S. PATENT DOCUMENTS

P.P. 3,845 3/1976 McGredy, IV ..... Plt./11

P.P. 4,798 1/1982 Kordes ..... Plt./11

P.P. 5,729 4/1986 Kriloff ..... Plt./11

*Primary Examiner*—Howard J. Locker

*Attorney, Agent, or Firm*—Klarquist Sparkman Campbell Leigh & Whinston

[57] ABSTRACT

A new and distinct variety of rose plant of the Hybrid Tea class, substantially as herein shown and described, characterized particularly as to novelty by the unique combination of its bicolor flower, few thorns, resistance to powdery mildew, good production as a cut flower greenhouse rose and vigorous, upright habit of growth.

1 Drawing Sheet

The present invention relates to a new and distinct variety of rose plant of the Hybrid Tea class which was originated by me by crossing the variety Merko, U.S. Plant Pat. No. 3,724, with the variety AROfiric, unpatented.

The primary objective of this breeding was to produce a new rose variety having the orange color, excellent vase life and production of the female parent, combined with the bicolor effect, glossy foliage and good production of the male parent. These objectives were substantially achieved, along with other desirable improvements, as evidenced by the following unique combination of characteristics that are outstanding in the new variety and that distinguish it from its parents, as well as from all other varieties of which I am aware:

1. Bicolor flower;
2. Few thorns;
3. Resistance to powdery mildew;
4. Good production (200 stems per square meter) as a cut flower greenhouse rose; and
5. Vigorous, upright habit of growth.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Merko.

*Pollen parent.*—AROfiric.

Classification:

*Botanical.*—*Rosa hybrida.*

*Commercial.*—Hybrid Tea.

FLOWER

Observations made from specimens grown in a greenhouse environment at Somis, Calif.

Blooming habit: Continuous.

Bud:

*Size.*—1½ inches long when the petals start to unfurl.

*Form.*—The bud form is long, pointed ovoid.

*Color.*—When sepals first divide, bud color is Orange White Group 159D with the tip and edges of the petals being Red Group 40A. When half blown, the upper sides of the petals are Red Group 40A; and the lower sides of the petals are Orange White Group 159A.

*Sepals.*—Color: Green Group 138B. Surface texture: Covered in fine hairs. There are three normally appendaged sepals. There are two unappendaged sepals with hairy edges.

*Receptacle.*—Color: Green Group 138A. Shape: Funnel. Size: Small to medium (⅜ inch wide×⅝ inch long). Surface: Smooth.

*Peduncle.*—Length: Short (1½ inches to 2 inches). Surface: Smooth, with a few glands. Color: Medium green. Strength: Stiff, erect.

Bloom:

*Size.*—Medium. Average open size is 4 inches.

*Borne.*—Singly.

*Stems.*—Medium, strong. Average length is about 22 inches to 24 inches.

*Form.*—When first open: High centered. Permanence: Flattens, outer petals curl back.

*Petalage.*—Number of petals under normal conditions: 30 to 35.

*Color.*—The upper side of the petals is Red Group 40A. The reverse side of the petals is Orange-White Group 159A with the tip and edges being Red Group 40A. The base of each petal has a small (¼ inch×¼ inch) half moon at the point of attachment which is Yellow Group 8B. The major color on the upper side is Red Group 40A.

*Variegations.*—Occasional white streak on the guard petals.

*Discoloration.*—The general tonality at the end of the first day: No change. At the end of the third day, no change. By the fifth day there is a fading on the plant to Red Group 40B. By the seventh day, fading to Red Group 40C.

*Fragrance.*—Slight.

Petals:

*Texture.*—Thick.

*Shape.*—Round.

*Form.*—Tips slightly recurved.

*Arrangement.*—Imbricated, with a few petaloids in the center.

*Persistence.*—Drop off cleanly.

*Lastingness.*—On the plant: Long (7 to 8 days). As a cut flower: Long (9 to 10 days).

Reproductive parts:

*Anthers.*—Size: Medium. Quantity: Many. Color: Yellow. Arrangement: Regular around styles.

*Filaments.*—Color: yellow.

*Pollen.*—Color: Gold yellow.

*Styles.*—Color: Red.

*Stigmas.*—Color: Greenish white.

Form: Bush.

Growth: Vigorous, upright, branching; in a greenhouse, the average plant will be 6 feet tall and 4 feet wide.

Foliage:

*Number of leaflets on normal mid-stem leaves.*— 5.

*Size.*—Large (6 inches×4 inches).

*Quantity.*—Abundant.

*Color.*—New foliage: Reddish Greyed Purple 183C. Old foliage: Green Group 136B on the upper side, and Green Group 136C on the lower side.

Leaflets:

*Shape.*—Broadly oval.

*Texture.*—Upper side: Leathery.

*Edge.*—Serrated.

*Serration.*—Single, small.

*Petiole rachis.*—Color: Green.

*Petiole underside.*—Smooth, with an occasional prickle.

*Stipules.*—Medium, serrated, bearded.

*Disease resistance.*—Resistant to mildew under normal growing conditions in a greenhouse in Somis, Calif.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Medium, hooked downward.

*Color when young.*—Red.

Small prickles:

*Quantity.*—On main stalks: None. On laterals: None.

I claim:

1. A new and distinct variety of rose plant of the Hybrid Tea class, substantially as herein shown and described, characterized particularly as to novelty by the unique combination of its bicolor flower, few thorns, resistance to powdery mildew, good production as a cut flower greenhouse rose and vigorous, upright habit of growth.

* * * * *

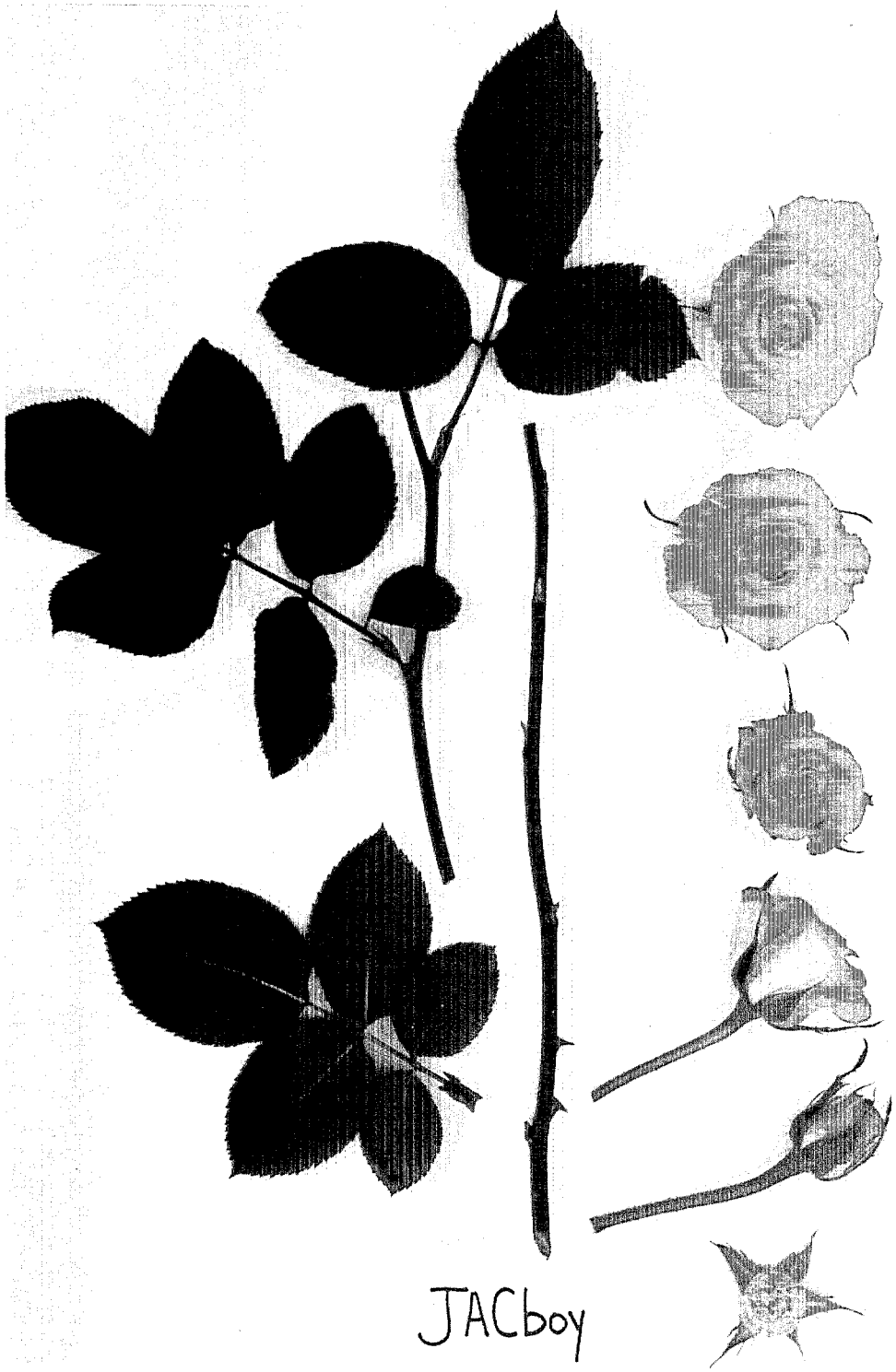
JACboy